United States Patent
Su et al.

(10) Patent No.: US 7,304,183 B2
(45) Date of Patent: Dec. 4, 2007

(54) CO-PRODUCTION OF CYCLOHEXYLAMINE AND BIS(PARA-AMINOCYCLOHEXYL) METHANE

(75) Inventors: Wei-Yang Su, Spring, TX (US); Ralph M. DiGuilio, Spring, TX (US); Pete S. Morford, Austin, TX (US)

(73) Assignee: Huntsman Petrochemical Corporation, The Woodlands, TX (US)

( * ) Notice: Subject to any disclaimer, the term of this patent is extended or adjusted under 35 U.S.C. 154(b) by 85 days.

(21) Appl. No.: 11/300,991

(22) Filed: Dec. 15, 2005

(65) Prior Publication Data

US 2006/0135814 A1     Jun. 22, 2006

Related U.S. Application Data

(60) Provisional application No. 60/636,759, filed on Dec. 16, 2004.

(51) Int. Cl.
*C07C 209/72*     (2006.01)
(52) U.S. Cl. ...................................... 564/451
(58) Field of Classification Search ................ 564/451
See application file for complete search history.

(56) References Cited

U.S. PATENT DOCUMENTS

| | | | |
|---|---|---|---|
| 3,347,917 A | 10/1967 | Arthur | |
| 3,558,703 A * | 1/1971 | Adam et al. | 564/451 |
| 3,591,635 A | 7/1971 | Farrissey et al. | |
| 3,636,108 A | 1/1972 | Brake | |
| 3,644,522 A | 2/1972 | Brake et al. | |
| 3,766,272 A | 10/1973 | Brake | |
| 3,856,862 A | 12/1974 | Chung et al. | |
| 3,959,374 A | 5/1976 | Brennan et al. | |
| 4,448,995 A | 5/1984 | Allen | |
| 4,754,070 A | 6/1988 | Casey et al. | |
| 4,946,998 A | 8/1990 | Casey et al. | |
| 5,214,212 A | 5/1993 | Whitman | |
| 5,245,082 A | 9/1993 | Immel et al. | |
| 5,296,560 A | 3/1994 | Gutierrez et al. | |
| 5,550,294 A | 8/1996 | Whitman | |
| 5,578,237 A | 11/1996 | Emert et al. | |
| 5,578,546 A | 11/1996 | Maschmeyer et al. | |
| 5,741,929 A | 4/1998 | Darsow et al. | |
| 6,184,416 B1 | 2/2001 | Ding et al. | |
| 6,248,924 B1 | 6/2001 | Ruhl et al. | |

OTHER PUBLICATIONS

The Merck Index 12th ed. (1996), S. Budavari ed., Merck & Co., Inc., Whitehouse Station, NJ, p. 1157-1158, entry No. 6831.*

* cited by examiner

*Primary Examiner*—Brian Davis
(74) *Attorney, Agent, or Firm*—Ron D. Brown; Edward D. Korompai

(57) ABSTRACT

Embodiments of the present invention disclose a process for the co-production of bis(para-aminocyclohexyl) methane (PACM). Also disclosed are articles of manufacture made using PACM produced by methods of this invention. The methods of the present invention generally include a first mixture having methylene di-aniline (MDA) and a second aromatic amine. The first mixture has less than 15% polymeric MDA by weight and the second aromatic amine is present in an amount to render the first mixture a liquid. The first mixture is hydrogenated to produce a product mixture comprising PACM and at least one second non-aromatic amine.

22 Claims, No Drawings

CO-PRODUCTION OF CYCLOHEXYLAMINE AND BIS(PARA-AMINOCYCLOHEXYL) METHANE

This application claims priority to US Provisional Patent Application No. 60/636,759 which was filed on Dec. 16, 2004 and which is currently still pending.

FIELD OF THE INVENTION

The present invention relates to an improved process to co-produce bis(para-aminocyclohexyl) methane ("PACM") from a mixture of methylene di-aniline (MDA) and a second aromatic amine. In particular, embodiments of this invention allow more efficient processes for producing PACM and more control over the isomer content of the PACM.

BACKGROUND INFORMATION

PACM is traditionally made from MDA via hydrogenation. Methods of making PACM typically include using a MDA feed that includes mixtures of MDA and co-products such as polymeric MDA. This MDA feed with polymeric MDA impurities comes from isocyanate plants that react aniline with formaldehyde to produce the MDA and polymeric MDA. Typically these co-products are then phosogenated to produce methyl diphenyl diisocyanate (MDI) and polymeric MDI. However, if these co-products are recovered before the phosogenation stage they may be used as a MDA feed that is hydrogenated to produce PACM. This feed is typically 60% to 85% MDA and 15% to 40% polymeric MDA. High polymeric MDA is undesirable in the feed when producing PACM because the polymeric MDA results in more unwanted products and the polymeric MDA will typically deactivate the catalyst used in the hydrogenation reaction. In order to decrease the polymeric MDA content of the feed, an operator may remove the polymeric MDA by such methods as distillation. The operator may also add pure MDA to dilute the polymeric MDA content of the feed. However, these techniques to increase the MDA content also increase production time and costs. Therefore, one disadvantage of current PACM processes is that the MDA feeds have relatively high levels of polymeric MDA.

In addition to the disadvantages listed above, traditional processes to produce PACM also typically require the use of solvents. Adding and removing additional solvents increases the cost, time and operational resources needed for the reaction. Lastly, processes that produce PACM typically have chemicals in multiple phases (e.g. a solid MDA and a liquid solvent). This creates inefficiencies in the process by increasing handling problems.

PACM has been used widely in many industries. When PACM is produced it has three positional isomers: trans-trans, cis-trans, and cis-cis. For certain industrial applications, it is important to limit the amount of certain isomers present. For example, to have an easily handling product with better performance in epoxy end-use applications, it is important to limit the amount of trans-trans isomer present. Many known processes produce PACM with isomer contents that are not useful for these applications and many processes have the drawback of only producing PACM with fixed isomer contents.

SUMMARY OF THE INVENTION

Embodiments of the present invention include a process for the co-production of PACM which provides a first mixture having MDA and at least one second aromatic amine. The first mixture has less than 15% by weight polymeric MDA. The second aromatic amine is present in an amount to render the first mixture a liquid. The first mixture is hydrogenated to produce a product mixture having PACM and at least one second non-aromatic amine. Further embodiments may separate the PACM from the product mixture.

Embodiments of the present invention have the advantages of a MDA feed with reactants already in a liquid phase. Additionally, the MDA feeds may have minimal polymeric MDA content, allowing purer product and less catalyst deactivation. The processes may also be controlled to allow a desired isomer content in the PACM product.

Embodiments of the present invention also include articles of manufacture that use PACM produced by the above processes. These articles may include nylons, nylons blends, fabrics, films, molded materials, epoxies, polyurethanes, coatings, lacquers, dispersants, oil additives, viscosity improvers, powder coatings and cosmetic compositions.

DETAILED DESCRIPTION OF THE INVENTION

Embodiments of the present invention describe a process for the co-production of PACM. The process includes taking a first mixture that has MDA and at least one second aromatic amine. The first mixture has less than 15% by weight polymeric MDA. The second aromatic amine is present in an amount to render the first mixture a liquid. The first mixture is hydrogenated to produce a product mixture comprising PACM and at least one second non-aromatic amine.

The first mixture includes MDA as well as expected derivatives and impurities present in MDA. The MDA may be derived from the reaction of aniline with formaldehyde. One skilled in the art will recognize other possible sources of MDA for use with this invention.

The first mixture may also include polymeric MDA. During the reaction of aniline and formaldehyde, not only is MDA formed, but also amounts of polymeric MDA are typically formed. Polymeric MDA is the result of the MDA molecule continuing to react with the aniline. Polymeric MDA materials typically present contain three or more aromatic rings. Because the hydrogenation of polymeric MDA does not significantly contribute to the PACM product produced and the polymeric MDA has a deactivating effect on the hydrogenating catalyst, it may be desirable to limit the amount of Polymeric MDA. Embodiments of the present invention have less than about 20%, 15%, 12%, 10%, 8%, 5%, 4%, 3%, 2% or 1% of polymeric MDA by weight of the first mixture, including all percentages below 20%. In one embodiment, the polymeric MDA is less than 15%. In a preferred embodiment, the first mixture has a minimal to no polymeric MDA present. For the purposes of this application, minimal shall mean less than 0.01% by weight of the first mixture.

The first mixture also includes at least one second aromatic amine. In embodiments of the present invention, the second aromatic amine has the benefit as serving as a solvent, thereby reducing the need for an additional solvent in the reaction. In some embodiments of the present invention, the second aromatic amine comprises aniline and expected derivatives and impurities found in aniline. One skilled in the art, with the benefit of this disclosure, will recognize other suitable second aromatic amines for use in this invention.

The at least one second aromatic amine is present in the first mixture in an amount to render the first mixture a liquid. This amount may be around 40-50% by weight of the first mixture, however, it may be lower depending on the temperature of the first mixture. MDA is typically a solid at standard temperature and pressure. However, the second aromatic amine acts a solvent to dissolve the MDA, making the first mixture easier to handle. In a further embodiment, the first mixture is a liquid at ambient temperature.

As discussed by the examples below, the amount of second aromatic amine used may influence the isomer content (trans-trans, trans-cis, or cis-cis) of PACM produced. In embodiments of the present invention, the second aromatic amine is present in an amount of at least about 30%, 50%, or 70% by weight based on the total weight of the first mixture, including all percentages above 30%. In further embodiments, the second aromatic amine is present in the first mixture in an amount effective for modifying the isomer content to be less than 25% by weight of the trans-trans isomer of PACM, based on the total weight of all isomers of PACM present in the product mixture. Adjusting the aniline content in the first mixture may also have the advantage of increasing the rate of hydrogenation of the MDA. Comparing Run #1 (1:1 MDA/aniline) in Table 1 to Run #1 (3:7 MDA/aniline) in Table 2 shows that the percentage of MDA in the solution after the reaction has decreased from 2.25% to 0.2%. Therefore, increasing the aniline content may act to increase the hydrogenation rate and to decrease the amount of un-reacted MDA. One skilled in the art, with the benefit of this disclosure, will recognize how to adjust the amount of the second aromatic amine in order to produce a desired PACM isomer ratio or amount of un-reacted MDA.

In embodiments of the present invention, the first mixture may be obtained from a stream of an isocyanate plant. In a preferred embodiment, the stream is a recycle stream of aniline, methylene di-aniline and derivatives thereof. This recycle stream recovers un-reacted aniline from the reaction of aniline and formaldehyde to produce MDA and polymeric MDA. This recycle stream typically has a very low polymeric MDA content and is typically already in a liquid phase, therefore allowing easier processing and reducing the need for additional solvents. Using a recycle stream, an operator may be able to selectively choose the aniline content of the first mixture, thereby having the ability to influence the isomers of PACM produced. One skilled in the art, with the benefit of this disclosure, will recognize other suitable sources of a first mixture.

In embodiments of the present invention, the first mixture is hydrogenated to produce PACM and a second aromatic amine. A catalyst may be used for the hydrogenation. The catalyst may be iron, cobalt, nickel, ruthenium, titanium, palladium, rhodium, platinum, iridium and combinations thereof. In other embodiments of the present invention, the catalyst is supported on at least one inert carrier. The inert carriers may be alumina, silicas, silicates, aluminosilicates, magnesiosilicates, clays and combinations thereof. In one embodiment of the present invention, the preferred catalyst is ruthenium on alumina which is available from Huntsman International LLC of The Woodlands, Tex. For this hydrogenation a hydrogen feed may be used. According to embodiments of the present invention, the hydrogenation may occur at any temperature in the range of between about 75° C. to about 200° C. Some preferred temperature ranges may be in the range of between about 90° C. to about 130° C. or in the range of between about 105° C. to about 115° C. The hydrogenation according to the present invention may be carried out at any pressure in the range of about 200 to about 5000 pounds per square inch gauge (psig), with about 1500 to about 2500 psig being preferable. One skilled in the art, with the benefit of this disclosure will recognize other suitable methods of hydrogenating the first mixture.

By manipulating variables of the hydrogenation reaction, the isomers of PACM produced may be selectively controlled. In particular, the aniline concentration, feed rate and temperature can be varied, alone or in combination, to produce a PACM with a desired isomer ratio. As stated above, the aniline content may be used to vary the isomer content of the PACM produced. The feed rate may also be adjusted to control the PACM isomers produced. The examples below show that a higher feed rate, resulting in shorter residence time may reduce the amount of trans-trans isomer produced. For the production of PACM with a higher trans-trans isomer ratio a slower feed rate, resulting in a longer residence time, may be preferable. Additionally, adjusting the temperature of the hydrogenation may influence the isomers of PACM produced. As described in the examples below, lower temperature may lead to a lower trans-trans isomer produced.

The hydrogenation produces a product mixture that has PACM and a second non-aromatic amine. The second non-aromatic amine may be cyclohexyl amine (CHA) and/or dicyclohexyl amine (DCHA). In another embodiment of the present invention, the CHA product is further reacted to produce DCHA. Although listed above are CHA and DCHA, one skilled in the art will recognize other CHA derivatives, DCHA derivatives, impurities and other chemical anomalies that would exist for such a reaction.

Once the product mixture has produced, the PACM, second aromatic amine, CHA, and/or DCHA may be separated from the product mixture. This may be done by known methods in the art such as distillation or crystallization. One skilled in the art with the benefit of this disclosure will recognize other suitable methods to separate the products.

PACM produced by embodiments of the present invention may be used in a variety of applications. One use of PACM is for the production of various nylons. These nylons are typically created by reacting PACM with a di-acid such as sebacic acid or adipic acid. These nylons may be used alone or blended with other nylons, thermoplastic materials, polycarbonates, and/or natural fibers in order to produce such items as fabrics, films and molded articles. PACM can also be used in various epoxy applications; for example, PACM may be used as curing agents and impregnants.

PACM produced by embodiments of the present invention may be used in polyurethanes. PACM may be used, without limitation, as precursors for isocyanate, chain extenders and/or viscosity agents. These urethanes may be used as urethane coatings and lacquers. PACM finds additional use as dispersants, viscosity improvers and as other additives for lubricating oils and other materials. Lastly, PACM produced by embodiments of the present invention may be used in powder coatings and cosmetic compositions.

EXAMPLE I

MDA/Aniline (1:1 by wt) Hydrogenation

To a tubular reactor filled with 200 cubic centimeters (cc) of glass beads on the bottom served as a preheat zone and 300 cc of a 1% ruthenium/alumina catalyst (commercially available from the Engelhard Corporation of Iselin, N.J.) was fed a mixture of aniline and methylene dianiline (1 to 1 by weight) and hydrogen at 2000 psig continuously. Various temperatures and feed rates were evaluated. The reactor effluent was analyzed by gas chromatography. The results are in Table 1 below. Cyclohexylamine is abbreviated as "CHA" and dicyclohexylamine is abbreviated as "DCHA".

TABLE 1

MDA/Aniline (1 to 1 by weight) Hydrogenation
1% Ru on Alumina

| Run # | Feed Rate | RX Temp, C. | Hot Spot, C. | CHA | DCHA | Aniline | PACM, GC A % trans-trans | cis-trans | cis-cis | MDA |
|---|---|---|---|---|---|---|---|---|---|---|
| 1 | 60 g/hr | 110 | 123 | 44.39 | 2.89 | 0 | 5.38 | 14.17 | 10.96 | 2.25 |
| 2 | 60 g/hr | 120 | 136 | 44.48 | 2.68 | 0 | 12.55 | 22.57 | 11.88 | 0 |
| 3 | 60 g/hr | 130 | 147 | 45.49 | 2.8 | 0 | 18.2 | 21.4 | 7.94 | 0 |
| 4 | 30 g/hr | 110 | 117 | 40.47 | 2.67 | 0.13 | 11.38 | 22.65 | 12.91 | 0.24 |

The above results indicate that at higher temperature, higher trans-trans isomer PACM product would be obtained. However, by lowering both the feed rate and temperature, a lower trans-trans isomer PACM may be obtained composition of PACM can be achieved.

EXAMPLE II

Preparation of PACM

About 2800 grams (gm) of reactor effluent were collected from Run #4 in Table 1. About 1571 gm of the mixture was fractionally distilled. About 624.34 gm of cyclohexylamine and 760.66 gm of colorless liquid PACM were recovered at room temperature. The gas chromatography analysis showed that the PACM obtained contained 21.86% trans-trans isomer, 44.40% cis-trans isomer, and 33.74% cis-cis isomers.

EXAMPLE III

MDA/Aniline (3:7 by wt) Hydrogenation

The procedure of Example I was followed except that a MDA/aniline feed (3 to 7 by weight) was used. The results are in Table 2 below. These results suggest that higher net PACM product rate with desired isomers ratio could be achieved by increasing the aniline concentration.

TABLE 2

MDA/Aniline (3 to 7 by weight) Hydrogenation
1% Ru on Alumina

| Run # | Feed Rate | RX Temp, C. | Hot Spot, C. | CHA | DCHA | Aniline | PACM, GC A % trans-trans | cis-trans | cis-cis | MDA |
|---|---|---|---|---|---|---|---|---|---|---|
| 1 | 60 g/hr | 110 | 128 | 59.37 | 4.63 | 0.09 | 6.53 | 13.85 | 8.31 | 0.2 |
| 2 | 60 g/hr | 115 | 132 | 66.59 | 4.12 | 0.02 | 6.73 | 12.42 | 6.55 | 0.04 |

What is claimed is:

1. A process for the co-production of bis(para-aminocyclohexyl) methane which comprises the steps of:
   providing a first mixture having methylene di-aniline and at least one second aromatic amine,
      wherein the at least one second aromatic amine is present in an amount to render the first mixture a liquid, and
      wherein the first mixture has less than 15% polymeric methylene di-aniline by weight based on the total weight of the first mixture; and
   hydrogenating the first mixture to produce a product mixture comprising bis(para-aminocyclohexyl) methane and at least one second non-aromatic amine.

2. A process according to claim 1 further comprising separating the product mixture to recover bis(para-aminocyclohexyl) methane from the product mixture.

3. A process according to claim 1 further comprising separating the product mixture to recover the at least one second non-aromatic amine from the product mixture.

4. A process according to claim 1 wherein the first mixture is liquid at ambient temperature.

5. A process according to claim 1 wherein the at least one second aromatic amine comprises aniline.

6. A process according to claim 5 wherein the at least one second non-aromatic amine comprises cyclohexyl amine.

7. A process according to claim 5 wherein the second non-aromatic amine comprises dicyclohexyl amine.

8. A process according to claim 1 wherein the first mixture comprises a stream extracted from an isocyanate plant.

9. A process according to claim 1 wherein the first mixture comprises a recycle stream of aniline and methylene di-aniline.

10. A process according to claim 9 wherein the recycle stream recovers unreacted aniline from a reaction of aniline and formaldehyde to produce methylene di-aniline and polymeric methylene di-aniline.

11. A process according to claim 1 wherein the at least one second aromatic amine is present in an amount of at least about 30% by weight based on the total weight of the first mixture.

12. A process according to claim 1 wherein the at least one second aromatic amine is present in an amount of at least about 50% by weight based on the total weight of the first mixture.

13. A process according to claim 1 wherein the at least one second aromatic amine is present in an amount of at least about 70% by weight based on the total weight of the first mixture.

14. A process according to claim 1 wherein the first mixture has less than about 5% polymeric methylene di-aniline by weight of the first mixture.

15. A process according to claim 1 wherein the first mixture has less than about 1% polymeric methylene di-aniline by weight of the first mixture.

16. A process according to claim 1 wherein the first mixture contains less than about 0.01% polymeric methylene di-aniline by weight of the first mixture.

17. A process according to claim 1 wherein hydrogenating the first mixture comprises using a catalyst, wherein the catalyst is selected from group consisting of: iron, cobalt, nickel, ruthenium, titanium, palladium, rhodium, platinum, iridium and combinations thereof.

18. A process according to claim 17 wherein the catalyst is supported on at least one inert carrier.

19. A process according to claim 1 wherein the at least one second aromatic amine is present in the first mixture in an amount effective to modify the content of bis(para-aminocyclohexyl) methane to have less than 25% by weight of the trans-trans isomer of the bis(para-aminocyclohexyl) methane, based on the total weight of all isomers of bis(para-aminocyclohexyl) methane.

20. A process according to claim 1, wherein hydrogenating the first mixture occurs at a temperature of about 75° C. to about 200° C.

21. A process according to claim 1 wherein hydrogenating the first mixture occurs at a temperature of about 100° C. to about 130° C.

22. A process for the co-production of bis(para-aminocyclohexyl) methane which comprises the steps of:
   providing a first mixture having methylene di-aniline and aniline, wherein the first mixture has less than about 5% polymeric methylene di-aniline by weight based on the total weight of the first mixture and wherein the aniline is present in an amount to render the first mixture a liquid;
   hydrogenating the first mixture to produce a product mixture comprising bis(para-aminocyclohexyl) methane and cyclohexyl amine; and
   separating the product mixture to recover bis(para-aminocyclohexyl) methane from the product mixture.

* * * * *